United States Patent [19]

Bonnett et al.

[11] Patent Number: 4,992,257
[45] Date of Patent: Feb. 12, 1991

[54] DIHYDROPORPHYRINS AND METHOD OF TREATING TUMORS

[75] Inventors: Raymond Bonnett; Morris C. Berenbaum, both of London, England

[73] Assignee: Efamol Holdings PLC, Surrey, England

[21] Appl. No.: 317,984

[22] Filed: Mar. 2, 1989

[30] Foreign Application Priority Data

Mar. 11, 1988 [GB] United Kingdom ................ 8805849

[51] Int. Cl.$^5$ .................... A61K 31/40; A61K 49/00; C07D 487/22
[52] U.S. Cl. ........................................ 424/9; 514/183; 514/410; 540/145
[58] Field of Search ................ 540/145; 514/183, 410; 424/9

[56] References Cited

U.S. PATENT DOCUMENTS

| | | | |
|---|---|---|---|
| 2,740,794 | 4/1956 | Bonner | 540/145 |
| 3,076,813 | 2/1963 | Sharp | 540/145 |
| 3,687,863 | 8/1972 | Wacher | 540/145 |
| 3,920,692 | 11/1975 | Wiersdorff et al. | 540/145 |
| 4,330,637 | 5/1982 | Wong | 540/145 |

FOREIGN PATENT DOCUMENTS

| | | |
|---|---|---|
| 0127797 | 6/1984 | European Pat. Off. . |
| 0186962 | 7/1986 | European Pat. Off. ............ 514/183 |
| 0214839 | 3/1987 | European Pat. Off. . |
| 61-130220 | 6/1986 | Japan . |

OTHER PUBLICATIONS

Zanelli et al., "Synthetic Porphyrins", Brit. J. Radiol. 54, pp. 403–407 (1981).
Ciba Foundation Symposium, 1989, pp. 34 to 39.
Bonnett et al., Biochemistry J. 1989, 261 277–280.
Journal of the American Chemical Society, vol. 95, No. 17, Aug. 22, 1973, pp. 5738–5741, H. W. Whitlock et al., "Behavior of Di- and Tetrahydro . . . ".
Patent Abstracts of Japan, vol. 4, No. 190 (C-37) (672), Dec. 26, 1980, Journal of the American Chemical Society, vol. 91, No. 26, Dec. 17, 1969, pp. 7485–7489, H. Whitlock et al., "Diimide Reduction . . .".

Primary Examiner—Mukund J. Shah
Assistant Examiner—E. C. Ward
Attorney, Agent, or Firm—Nixon & Vanderhye

[57] ABSTRACT

This invention provides novel compounds for therapy of tumors susceptible to necrosis when an appropriate compound is administered followed by illumination with light of a wavelength absorbed by the compound, the compounds being dihydro porphyrins of the formula, or the corresponding tetra-hydro prophyrins:

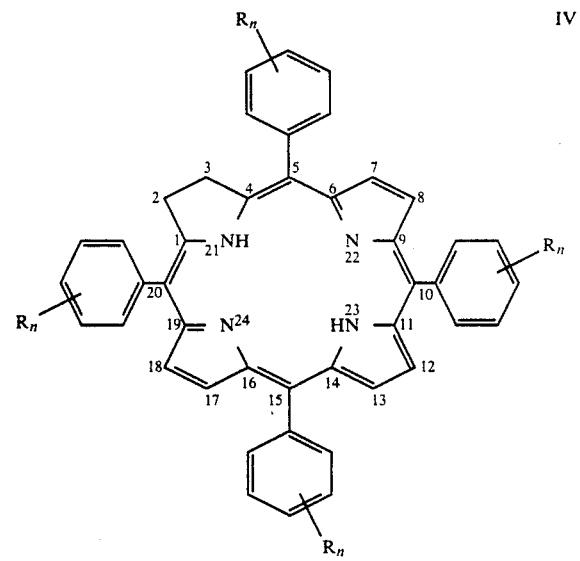

where n=1 to 3 and each substitutent R, the same or different and at the same or different position in its respective substituent phenyl ring, is an hydroxy group.

6 Claims, No Drawings

DIHYDROPORPHYRINS AND METHOD OF TREATING TUMORS

FIELD OF THE INVENTION

This invention relates to certain porphyrins and their use in cancer treatment.

BACKGROUND

Haematoporphyrin derivatives of uncertain specific composition (HpD) have been used in cancer treatment, having been found to locate in tumours and other tissues after injection into the bloodstream, and to sensitise cells to light irradiation (transport in the blood is believed to be largely in association with the serum albumin). Irradiation, with a laser or other source, may be direct or indirect, for example using fibre optics. Irradiated cells, unless deeply pigmented, are rapidly killed to a depth depending on the light penetration. The mechanism of cell killing in phototherapy is believed to be largely by production of singlet oxygen. This is produced by transfer of energy from the light-excited porphyrin molecule to an oxygen molecule. Singlet oxygen is highly reactive. It is believed to oxidise cell membranes so that they are damaged and become incapable of exerting their function of controlling the cell's internal operation. This rapidly leads to cell death.

Selectivity of damage for various tissues, including tumours, is governed by a variety of factors, including selective uptake, selective vulnerability and selective ability to repair damage (cf. Albert A.A. "Selective Toxicity", fifth edition, Chapman & Hall, London 1973). In tumours an additional factor is the precarious nature of tumour blood supply and its particular vulnerability to photo-dynamic damage as compared with the robust and well-established blood supply of normal tissues. All the above factors vary from one tissue to another and from one compound to another, so that the pattern of tumour and normal tissue damage may be expected to vary.

In EP-A-0,186,962, the present applicants made proposals to improve on HpD by finding well characterised and thus more exactly controllable compounds. Other aims were to find compounds activated by light at wavelengths longer than those used to activate HpD so as to exploit deeper penetration of longer wavelength radiation, and to increase effectiveness generally, as in many anatomical sites, such as the brain, HpD has been found to sensitise normal cells unduly as well as cancerous cells. The wavelength at which a photo-sensitising compound is activated is one factor in its in vivo effectiveness. Other things being equal, the longer the activating wavelength within the visible range, the greater the tissue penetration of light and therefore the greater the depth of damage. Thus, compounds activated at 650–660 nm might be expected to produce greater depths of damage than HpD, which is activated at 625–630 nm. Successful photo-therapy depends on the ability to produce severe tumour damage without unacceptable damage to contiguous normal tissues. The compounds used according to EP-A-0,186,962 are porphyrins tetra-meso-substituted by aromatic groups bearing hydroxy, amino or sulphydryl groups, some new as compounds others old.

The present invention also concerns medicaments for therapy of tumours susceptible to necrosis when an appropriate compound is administered to locate in the tumour followed by illumination of the tumour with light of a wavelength absorbed by the compound, but the compounds are new and the invention therefore lies primarily in them. They are dihydro porphyrins (chlorins) I, and corresponding tetra-hydro porphyrins II and III, of the formulae:

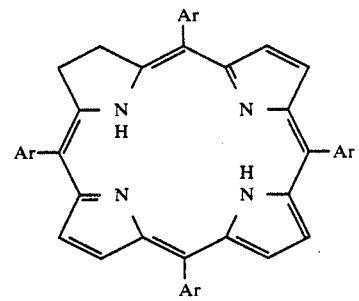

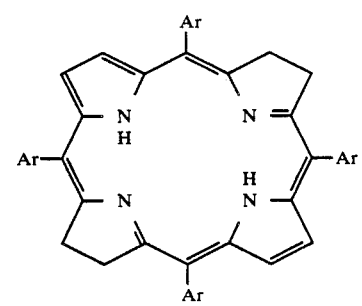

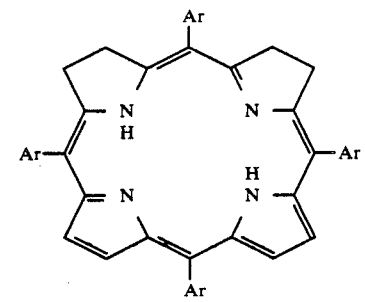

wherein each Ar, the same or different, is an aromatic group with one or more hydroxy (—OH) substituent groups For example, and showing the ring numbering, the dihydro porphyrins (and the tetra-hydro porphyrins correspondingly) may be:

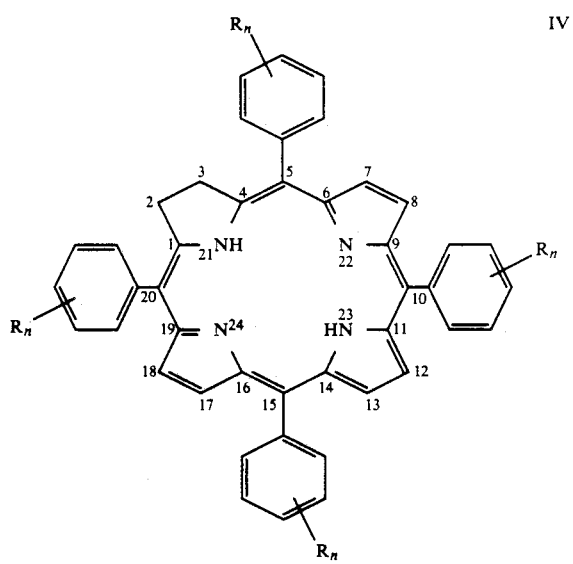

wherein each R (one or more in each ring n=1 to 3) is an ortho, meta or para positioned hydroxy substituent group, particularly to give polyhydroxyphenyl compounds Said substituent groups may be in the same or different positions on their respective aromatic groups. Any said substituent group may be free or itself substituted, for example by alkyl or acyl groups preferably $C_1$ to $C_4$ and the compounds when in such form are within the claims herein. The nucleus or the substituent rings may be substituted further, provided pharmacological tolerability, appreciable solubility in water (required so that the drug may be administered intravenously to ensure rapid distribution to the tumour), absorption of light at the red end of the spectrum, and take up in cancerous tissue are retained, and again the compounds when in such form are to be understood as within the claims herein.

Any of the compounds further may be in the form of derivatives such as salts at acidic or basic centres, metal complexes (e.g. Zn, Ga), or hydrates or other solvates particularly with lower, e.g. $C_1$–$C_4$ aliphatic alcohols and again such derivatives are within the claims.

It is preferred that one or more of the said substituent groups should be of a kind and in a form able to ionise at physiological pH, to increase the absorption in the red part of the spectrum, that is in the portion that most effectively penetrates tissue. Compounds not very soluble in themselves may be solubilised by the presence of suitable groups such as sulphonate groups.

The invention further extends to the medicaments, to their preparation and to the method of therapy itself.

Various specific compounds within the claims are given in Table 1 below:

TABLE 1

| NUMBER | NATURE OF "Ar" IN FORMULA I or II | CODE NAME (DIHYDRO or TETRA-HYDRO FORM OF) |
|---|---|---|
| 1 | —C6H4—OH (para) | HK7 |
| 2 | —C6H4—OC(O)CH3 (para) | acetyl HK7 |
| 3 | —C6H4—OH (ortho) | ortho-HK7 |
| 4 | —C6H4—OCH3 (ortho) | ortho-HK7 methyl ether |
| 5 | —C6H4—OH (meta) | meta-HK7 |
| 6 | —C6H4—OC(O)CH3 (meta) | acetyl meta-HK7 |

The invention is illustrated in the following Examples, in which the compounds are made by the reduction of the corresponding porphyrins, without protection of the latter. The general method of reduction is not new (Whitlock et al., J. Amer. Chem. Soc., 1969, 91, 7485) but the products are new. It is unexpected that they can be obtained without prior protection of phenolic hydroxy functions, especially when an oxidative step is required in the work up. When required, a chloranil dehydrogenation step is included to oxidise tetra-hydro porphyrins formed back to the dihydro form.

EXAMPLE 1

Synthesis of 2,3-dihydro-5,10,15,20-tetra(p-hydroxyphenyl) porphyrin ("Dihydro HK7")

5,10,15,20-Tetra(p-hydroxyphenyl)porphyrin (163 mg, 0.24 mmoles), p-toluenesulphonhydrazide (90 mg, 0.48 mmoles), anhydrous potassium carbonate (300 mg) and anhydrous pyridine (11.25 ml) were stirred with nitrogen flushing for 20 minutes. The mixture was heated (100°–105° C.) for 6.5 hours under nitrogen: further quantities of p-toluenesulphonhydrazide (97 mg in 0.3 ml anhydrous pyridine on each occasion) were added after 2 hours and 4 hours. The reaction mixture was treated with ethyl acetate (75 ml) and distilled water (37.5 ml) and digested on a steam bath for 1 hour. The organic layer was separated and washed in turn with hydrochloric acid (2M, 75 ml), distilled water (75 ml) and saturated sodium bicarbonate solution (75 ml).

o-Chloranil (total 166 mg, 0.675 mmoles) was added in portions to the stirred organic solution at room temperature until the absorption peak at 735 nm had disappeared.

The mixture was washed with aqueous sodium bisulphite (5%, 2×75 ml), distilled water (75 ml), sodium hydroxide (0.01M, 100 ml) and saturated sodium bicarbonate (80 ml) and dried over anhydrous sodium sulphate. The filtered solution was evaporated to dryness and the residue was crystallised from methanol-distilled water to give 77 mg (middle cut, 47%) of 2,3-dihydro-5,10,15,20-tetra(p-hydroxyphenyl)porphyrin as a $C_{44}H_{32}N_4O_4$ requires M+1=681.250. Nmr spectrum in accord with structure. Electronic spectrum $\lambda_{max}$ (MeOH) ($\epsilon$) 285 (17000), 295 (16900), 418 (143000), 520 (10000), 550 (9000), 597 (5100), and 651 (18600). $R_f$ 0.49 on Merck silica gel irrigated with MeOH:CHCl$_3$ (1:4).

EXAMPLE 2

Synthesis of
2,3-dihydro-5,10,15,20-tetra(m-hydroxyphenyl) porphyrin ("Dihydro meta-HK7")

The method was as described above starting with the following reagents: 5,10,15,20-tetra(m-hydroxyphenyl) porphyrin (160 mg, 0.23 mmoles), p-toluenesulphonhydrazide (90 mg, 0.48 mmoles), anhydrous potassium carbonate (303 mg), anhydrous pyridine (11.25 ml), and o-chloranil (106 mg, 0.43 mmoles).

The middle cut from the crystallisation from methanol-distilled water gave 59 mg (37%) of 2,3-dihydro-5,10,15,20-tetra(m-hydroxyphenyl)porphyrin as a purple solid. Mass spectrum (FAB) (M+H)$^+$681. $C_{44}H_{32}N_4O_4$ requires M 680. Electronic spectrum $\lambda_{max}$ (MeOH) ($\epsilon$) 284 (16900), 306 (15600), 415 (146000), 516 (11000) 543 (7300), 591 (4400), and 650 (22400). $R_f$ 0.52 on Merck silica gel irrigated with MeOH:CHCl$_3$ (1:4).

EXAMPLE 3

Synthesis of 2,3-dihydro-5,10,15,20-tetra (o-hydroxyphenyl) porphyrin ("Dihydro ortho-HK7")

The method was as described above starting with the following reagents: 5,10,15,20-tetra (o-hydroxyphenyl) porphyrin (163 mg, 0.24 m moles), anhydrous potassium carbonate (303 mg), anhydrous pyridine (11.25 ml), and o-chloranil (132 mg, 0.54 m moles).

Crystallisation from methanol-distilled water gave 105 mg (64%) of 2,3-dihydro-5,10,15,20 -tetra(o-hydroxyphenyl) porphyrin as a dark purple crystalline solid. It was a mixture of atropisomers (Rf 0.23, 0.29, 0.38 and 0.43 on silica gel irrigated with 1% MeOH in CHCl$_3$. Mass spectrum (FAB) (M+H)$^{30}$681. $C_{44}H_{32}N_4O_4$ requires M 680. Electronic spectrum $\lambda_{max}$ (MeOH) ($\epsilon$) 415 (90700), 515 (8400), 542 (5600), 597 (3800), and 651 (16000).

EXAMPLE 4

Synthesis of
7,8,17,18-tetrahydro-5,10,15,20-tetra(m-hydroxyphenyl) porphyrin 5,10,15,20-tetra(m-hydroxyphenyl)porphyrin (109 mg, 0.16 mmoles), p-toluenesulphonylhydrazide (60 mg), anhydrous potassium carbonate (200 mg) and anhydrous pyridine (7.5 ml) were stirred with nitrogen flushing for 20 min. The mixture was heated (100°–105° C.) for a total of 12 hours under nitrogen, further quantities of p-toluenesulphonylhydrazide being added every 1.5 hour (60 mg in 0.2 ml pyridine on each occasion). The reaction mixture was treated with ethyl acetate (100 ml) and water 50 ml) and digested on a steam bath for 1 hour. The organic layer was separated, and washed with hydrochloric acid (2M, 50 ml), and then with phosphoric acid (56%, 4 x 50 ml, to remove chlorin). The organic layer was washed in turn with distilled water (50 ml), sodium bicarbonate (50 ml), distilled water (50 ml), hydrochloric acid (2M, 50 ml), and distilled water (50 ml), and dried over anhydrous potassium carbonate. After filtration and removal of solvent the residue was crystallised from methanol-water to give the title compound as a green solid (29 mg, 27%). $R_f$ 0.47 on silica gel irrigated with MeOH-CHCl$_3$ (1:4).

$\lambda$(MeOH, nm) ($\epsilon$) 352 (92,000), 361 (114,000), 372 (129,000), 516 (50,000) and 735 (91,000).

$\delta$(d$_6$–DMSO) (250 MHz): −9.69 (s, 3.8H, OH); 7.95 (s, 4.0H, $\Delta$-pyrrole H), 7.47 (t, 5.2H, ArH); 7.21 (d, 4.2H, ArH); 7.18 (s, 4.2H, ArH; 7.04 (d, 4.0H, ArH); 3.95 (s, 7.5H, CH$_2$); and −1.54 (s, 2.0H, NH).

The activity of the compounds has been demonstrated in tests given in Table 2 below, the dihydro compounds being referred to as chlorins and the tetrahydro compounds as bacteriochlorins.

TABLE 2

Tumour photo-necrosis with chlorins (C) and a bacteriochlorin (BC) of the meso-tetra(hydroxyphenyl) (THP) series.

| Photo-sensitiser | Dose $\mu$M/Kg | Wavelength* (nm) | Depth of Tumour Necrosis mm ± SE** |
|---|---|---|---|
| p-THPC | 6.25 | 653 | 3.50 ± 0.54 (10) |
|  | 3.125 | 653 | 2.13 ± 0.50 (10) |
| m-THPC | 0.75 | 652 | 5.41 ± 0.39 (19) |
|  | 0.375 | 652 | 3.79 ± 0.28 (6) |
| o-THPC | 6.25 | 652 | 4.16 ± 0.27 (14) |
|  | 3.125 | 652 | 3.69 ± 0.74 (9) |
| m-THPBC | 0.39 | 741 | 5.22 ± 1.21 (8) |

*The total energy administered was 10 J cm$^{-2}$ throughout.
**Number of tumours in parenthesis.

the method of testing is that the PC6 plasma cell tumour, obtained initially from the Chester Beatty Research Institute, was grown by inoculating 0.3–0.6×10$^6$ cells subcutaneously in female BALB/c mice. It was used about two weeks later, when it was 12–13 nm in its longest diameter and 6–7 nm deep. Sensitisers were injected in dimethyl sulphoxide intra-peritoneally (2.5 ul g$^{-1}$) and, twenty four hours later, skin over the tumours was depilated, the mice anaesthetised and tumours exposed to 10 J cm$^{-2}$ light. Wavelengths for illumination were the longest wavelength absorption peaks in the red in solutions of sensitiser in fetal calf serum, and were 652–653 nm for the compounds of Examples 1 to 3 and 741 nm for the compound of Example 4. The light source was a copper vapour laser with an output of 10 to 12 watts (Cu 10 laser, Oxford Lasers Ltd) pumping a D2 10K dye laser (Oxford Lasers Ltd). The dye was rhodamine 640 (Applied Photophysics Ltd) for illumination at 652–653 nm and LDS-722 for illumination at 741 nm. Light intensity at the tumour surface was kept below 0.3 W cm$^{-2}$, where thermal effects were undetectable.

Twenty four hours after illumination at 652–653 nm and LDS 722 for illumination at 741 nm, 0.2 ml 1% Evans blue (Sigma) in saline was given intravenously and tumours were removed one hour later and fixed in formolsaline. The fixed tumours were sliced at right angles to the surface and the depth of necrosis measured with a dissecting microscope fitted with an eye piece graticule.

In preliminary tests the new compounds have shown similar results as regards skin sensitivity to those given in EP-A-0,186,962. Moreover, the para and meta dihydroxy compounds have been shown specifically, improved properties in other respects which may be expected in all the compounds. The results of a number of experiments are given in Tables 3 and 4 below.

TABLE 3

DEGREE OF TUMOUR NECROSIS OBTAINED AT AN EQUIVALENT MUSCLE DAMAGE LEVEL

| Muscle Oedema (% increase in muscle weight) | Tumour Necrosis (mm) | |
| --- | --- | --- |
| | Corresponding Compounds of EP-A-0186962 | Compounds of Examples 1 and 2 above |
| | Para | Para |
| 10% | 2.25 | 3.5 |
| 20% | 3.0 | 4.0 approx. |
| | Meta | Meta |
| 10% | 3.5 | 5.5–6 |
| 20% | 4.0 | 6.5 |

TABLE 4

COST IN TERMS OF MUSCLE DAMAGE FOR SPECIFIED DEPTHS OF TUMOUR NECROSIS

| Depth of Tumour Necrosis (mm) | Muscle Oedema (% Increase in Weight) | |
| --- | --- | --- |
| | Corresponding Compounds of EP-A-0186962 | Compounds of Examples 1 and 2 above |
| | Para | Para |
| 3.0 | 20 | 8 |
| 3.5 | 22 | 10 |
| | Meta | Meta |
| 3.5 | 10 | 2 |
| 4.0 | 20 | 3 |
| 5.0 | 36 | 5 |
| 5.5 | 49 | 7 |

CONCLUSION

Tables 3 and 4 show that, for specified levels of muscle damage, the compounds of Examples 1 and 2 produce more tumour necrosis than the corresponding compounds of EP-A-0,186,962 and, for specified levels of tumour necrosis, cause considerably less muscle damage than the corresponding compounds of EP-A-0,186,962.

This type of selectivity is particularly important in the photo-therapy of tumours in anatomical sites where muscle is a major constituent, e.g., in cancer of the head and neck, and in cancer of the large intestine and rectum with possible involvement of abdominal wall or pelvis.

In administration the compounds, as with known tumour sensitisers, will be given intravenously in a blood compatible preparation. Conveniently an aqueous solution is used but if water solubility is limited, a solution in an organic, non-toxic polar solvent such as ethanol or a mixture of such solvents may for example be prepared. A further route to water solubility in the sense of transport in the aqueous environment of the bloodstream is the preparation of liposomes to be administered in aqueous media. Therapy according to the invention is thus administered in suitable form in an amount determined by the general toxicity of the particular compound and its level of necrotic effect, allowing tumour location to take place, and illuminating with light of a wavelength reaching the tumour and exciting the compound, at a dose effecting tumour necrosis without unacceptably damaging normal tissue. All this is in per se known manner, not requiring detailed discussion on its optimisation.

We claim:

1. A compound of the formula:

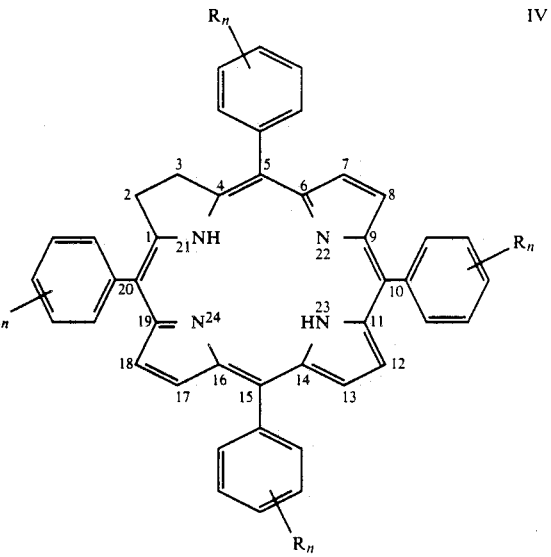

or the corresponding tetra-hydroporphyrins, where n—1 to 3 and each substituent R, which may be the same or different and at the same or different position in its respective substituent phenyl ring, is a hydroxy group or a hydroxy group substituted with a $C_{1-4}$ alkyl or $C_{1-4}$ acyl group.

2. A compound of the formula:

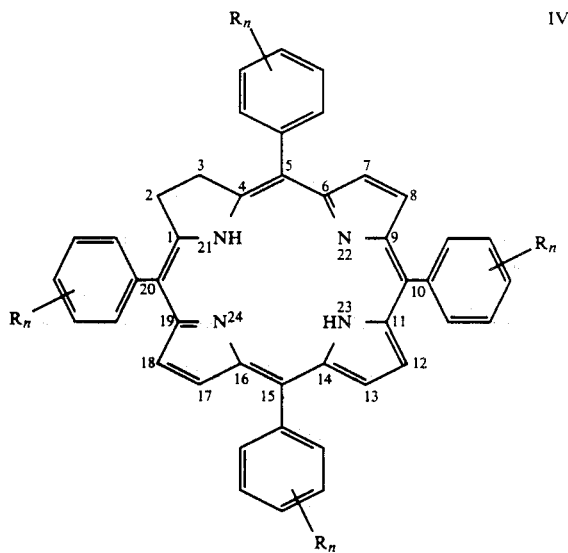

or the corresponding tetra-hydroporphyrins, where n=1 to 3 and each substituent R, which may be the same or different and at the same or different position in its respective substituent phenyl ring, is a hydroxy group.

3. A compound according to claim 1, wherein each group Ar is an o-hydroxyphenyl, m-hydroxyphenyl, or p-hydroxyphenyl group.

4. A compound according to claim 1, wherein each hydroxy substituent is in free rather than in a substituted form.

5. A compound
2,3-dihydro-5,10,15,20-tetra(p-hydroxy-phenyl) porphyrin;
2,3-dihydro-5,10,15,20-tetra(m-hydroxy-phenyl) porphyrin;
2,3-dihydro-5,10,15,10-tetra(o-hydroxy-phenyl) porphyrin; or
7,8,17,18-tetrahydro-5,10,15,10-tetra(m-hydroxy-phenyl) porphyrin.

6. A pharmaceutical composition for treating tumors comprising a tumor-locating porphyrin compound of claim 1, together with a pharmaceutically acceptable carrier or diluent.

* * * * *